(12) United States Patent
Hensley

(10) Patent No.: US 11,938,484 B2
(45) Date of Patent: Mar. 26, 2024

(54) UNIFORM FLUID FILM COOLING DEVICE

(71) Applicant: Canon Virginia, Inc., Newport News, VA (US)

(72) Inventor: Maxwell Hensley, Williamsburg, VA (US)

(73) Assignee: Canon Virginia, Inc., Newport News, VA (US)

( * ) Notice: Subject to any disclaimer, the term of this patent is extended or adjusted under 35 U.S.C. 154(b) by 269 days.

(21) Appl. No.: 17/244,419

(22) Filed: Apr. 29, 2021

(65) Prior Publication Data

US 2021/0339257 A1 Nov. 4, 2021

Related U.S. Application Data

(60) Provisional application No. 63/018,004, filed on Apr. 30, 2020.

(51) Int. Cl.
*B01L 7/00* (2006.01)
*C12Q 1/6844* (2018.01)
*F28C 3/00* (2006.01)

(52) U.S. Cl.
CPC .............. *B01L 7/52* (2013.01); *C12Q 1/6846* (2013.01); *F28C 3/00* (2013.01); *B01L 2300/1805* (2013.01); *B01L 2300/1838* (2013.01); *B01L 2300/1894* (2013.01)

(58) Field of Classification Search
None
See application file for complete search history.

(56) References Cited

U.S. PATENT DOCUMENTS

| | | | | |
|---|---|---|---|---|
| 5,066,377 A | * | 11/1991 | Rosenbaum | B01D 57/02 204/616 |
| 6,425,438 B1 | * | 7/2002 | Hahn | F28F 13/00 165/47 |
| 8,012,765 B2 | * | 9/2011 | Schembri | B01L 3/502707 435/286.7 |
| 2007/0281304 A1 | * | 12/2007 | Gianchandani | B01L 3/502761 435/7.1 |
| 2010/0112567 A1 | * | 5/2010 | Adolfsen | B01L 7/54 435/6.16 |
| 2011/0152108 A1 | * | 6/2011 | Brenan | C12Q 1/686 506/37 |
| 2012/0052560 A1 | * | 3/2012 | Knight | G01N 35/1095 435/286.1 |

* cited by examiner

*Primary Examiner* — Aaron A Priest
(74) *Attorney, Agent, or Firm* — Canon U.S.A., Inc., IP Division

(57) ABSTRACT

The present disclosure relates to devices and methods for rapidly and uniformly cooling thermal cycling systems comprising selectively heating or cooling a thermal boundary layer at the edge of a bulk fluid flow.

4 Claims, 4 Drawing Sheets

UNIFORM FLUID FILM COOLING DEVICE

PRIORITY AND INCORPORATION BY REFERENCE

The present application claims priority to U.S. Provisional Patent Application Ser. No. 63/018,004 filed Apr. 30, 2020, the disclosure of which is incorporated herein by reference in its entirety.

FIELD OF THE DISCLOSURE

The present disclosure relates to non-contact devices and methods for cooling thermal cycling systems, including in systems for reactions such as the polymerase chain reaction.

BACKGROUND

One of the most powerful and basic technologies to detect small quantities of nucleic acids is to replicate some or all of a nucleic acid sequence many times, and then analyze the amplification products. Polymerase chain reaction (PCR) is a well-known technique for amplifying deoxyribonucleic acid (DNA) which can produce millions of copies of DNA starting from a single template DNA molecule. PCR includes phases of denaturation, annealing, and extension, which phases are part of a cycle which is repeated so that at the end of the reaction there are enough copies to be detected and analyzed.

The PCR phases of denaturing, annealing, and extension occur at different temperatures and cause target DNA molecule samples to replicate themselves. Temperature cycling (thermal cycling) requirements vary with particular nucleic acid samples and assays. In the denaturing phase, a double stranded DNA (dsDNA) is separated into single stranded DNA (ssDNA) by the heating the DNA. During the annealing phase, primers are attached to the single stranded DNA molecules. Single stranded DNA molecules form double stranded DNA in the extension phase through specific bindings between nucleotides in the PCR solution and the single stranded DNA. Typical temperatures for PCR are 95° C. for denaturing, 55° C. for annealing, and 72° C. for extension. The temperature is held at each phase for a certain amount of time which may be a fraction of a second up to a few tens of seconds. The DNA is doubled at each cycle, and it typically takes 20 to 40 cycles to produce enough DNA for certain applications. To obtain a successful amplification with the desired yield of target product, the sample temperatures at the different phases must be accurately controlled.

High throughput approaches to performing PCR and other amplification reactions have are common and may involve amplification reactions in microfluidic devices, as well as methods for detecting and analyzing amplified nucleic acids in or on the devices.

Cooling mechanisms present in thermal cycling systems (including microfluidic systems) used for PCR and other thermal cycling reactions rely on multiple methods in order to provide both the speed in switching between temperatures and the uniformity of temperature required for successful reactions. The majority of these systems utilize heating and cooling mechanisms that are based on physical contact of the substrate or sample in question via a heat sink or thermoelectric device. The nature of this type of connection leads to an increase in the thermal mass of the system, which in turn also increases the heater power required to compensate accordingly. Conversely, non-contact methods, such as forced fluid convection can cool very rapidly but typically are not very uniform in temperature unless the fluid has been heated to the target temperature. In order to maintain the flow rate required for a given rate of cooling, the power needed to heat the entire cooling fluid to the target temperature can be larger than desired and/or not feasible.

In PCR reactions, the cooling speed and thermal gradient in the area of interest are critical physical characteristics to the functioning of the device. It is ideal to have the thermal gradient within a very small temperature range so the entire solution is heated evenly and the PCR reactions occur at the same time and rate everywhere in the reaction chamber. Cooling can be accomplished in many traditional ways, from using a heat sink to a Thermoelectric device. However, these methods are based on physical contact, which is subject to variations in surface contact quality that can introduce additional complications to a system.

An alternate, non-contact method can be to use a cooling medium such as a gas or liquid to carry heat away from the surface via forced convective cooling. However, when used with a system utilizing a microfluidic chip, forced convection can result in local temperature gradients across the surface of the chip due to stagnation of impinging jets or the inherent thermal boundary layer formation when fluid flows parallel across the surface. To counter this gradient with forced convection, heating of the bulk fluid to the end point or goal temperature before flowing it over the surface can help to prevent thermal overshoot of the desired temperature. However, in the latter method, in order to achieve a fast cooling time, higher flow rates are required, which in turn need appreciably more power to be added to the fluid, thus negatively impacting efficiency, size of the device and the subsequent total power requirements. Therefore, a non-contact method for rapidly cooling thin film substrates with low power consumption, fast cooling speed, and high degree of uniformity is desired.

SUMMARY OF THE DISCLOSURE

The present disclosure relates to a device and method for regulating heating and cooling of a substrate in a thermal cycling system using a thermal boundary layer. Thus, in one aspect, the present disclosure provides a fluidic device comprising a substrate, wherein the substrate comprises at least one reaction chamber; a first heating element; and, a second heating element; means for providing a fluid flow that is flowed along one side of the substrate providing a thin fluid film; wherein the thin fluid film is in thermal communication with the substrate; wherein the first heating element applies heat to the substrate, and, wherein the second heating element is in thermal communication with the thin fluid film.

In a second aspect, the second heating element is incorporated in the fluid flow upstream of the first heating element. The second heating element can be located on the same side of the substrate as the thin fluid film.

In a third aspect, the thin fluid film comprises a thermal boundary layer adjacent to a surface of the substrate. In one aspect, increasing the temperature of the fluid regulates the cooling of the substrate.

In a fourth aspect, there is provided method for cooling a substrate, comprising the steps of: (i) heating a substrate by turning on a primary heating element, which primary heating element is turned off when the substrate is heated to the desired temperature; and (ii) causing a fluid having a lower temperature than the substrate to flow over at least one surface of the substrate, causing a thermal boundary layer to form. The thermal boundary layer can cause the substrate to cool rapidly.

In a further aspect, the method can additionally comprises the steps of (iii) providing a secondary heating element located upstream of the substrate; (iv) causing the secondary heating element to heat the fluid flowing over the substrate such that the temperature of the thermal boundary layer is increased, and (v) turning off the secondary heating element after the desired substrate temperature is reached.

In another aspect, the method steps can be repeated sequentially in order to provide thermal cycling of the substrate. Thermal cycling can occur until amplification of a nucleic acid sample occurs.

These and other embodiments, objects, features, and advantages of the present disclosure will become apparent upon reading the following detailed description of exemplary embodiments of the present disclosure, when taken in conjunction with the appended drawings, and provided claims.

BRIEF DESCRIPTION OF THE DRAWINGS

The accompanying drawings, which are incorporated herein and form part of the specification, illustrate various embodiments, objects, features, and advantages of the present disclosure.

Figure 1:
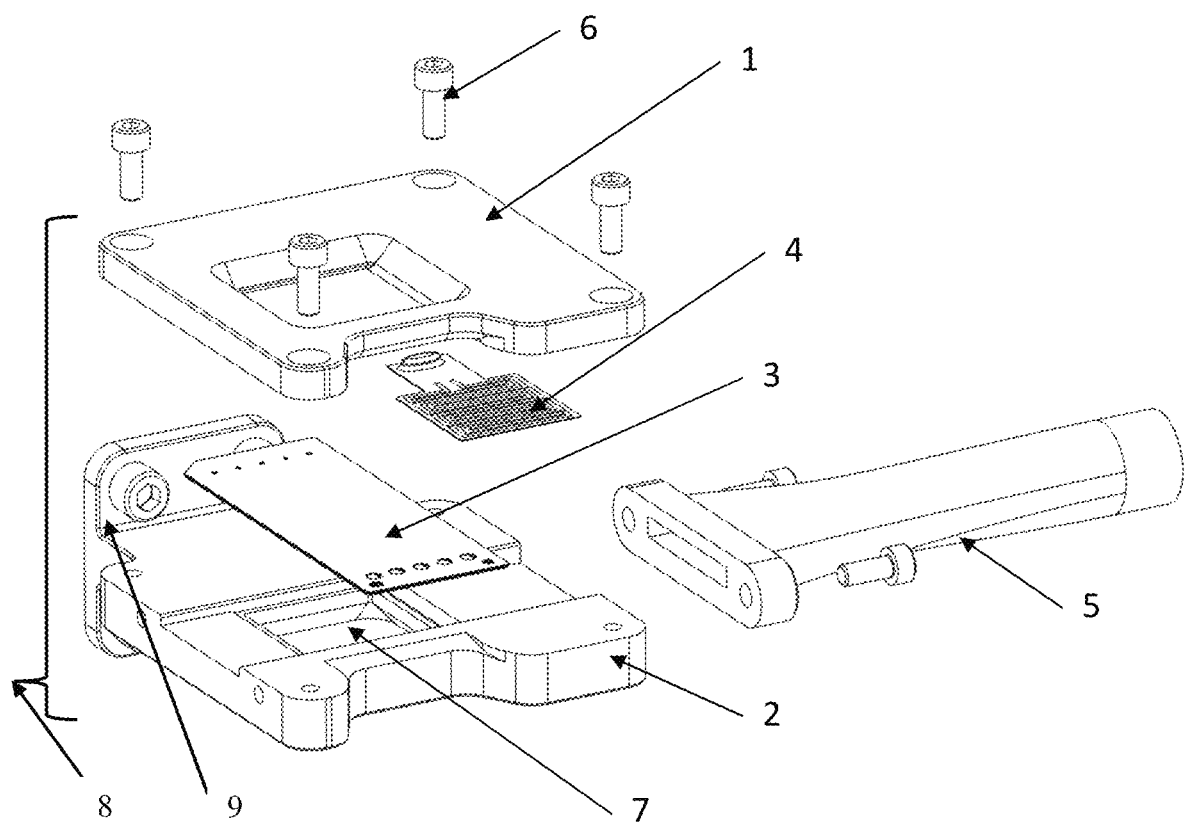
FIG. 1 is an exploded view of an exemplary device including a cartridge holder and a cooling stream directed at a microfluidic cartridge within the cartridge holder.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENT

The present disclosure has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The present disclosure is directed to methods and devices that will minimize undesirable thermal gradients in devices that perform PCR or other thermal cycling reactions, while also lowering power consumption, increasing the cooling speed and decreasing the size of the device.

To accomplish this, the present disclosure provides a device and method wherein a preheating element is located upstream of the substrate or cartridge on which the thermal cycling assay will be run, such that the preheating element heats a thin fluid film near the cartridge, known as a thermal boundary layer, to the desired temperature, rather than heating the entire fluid flow stream.

Figure 2:
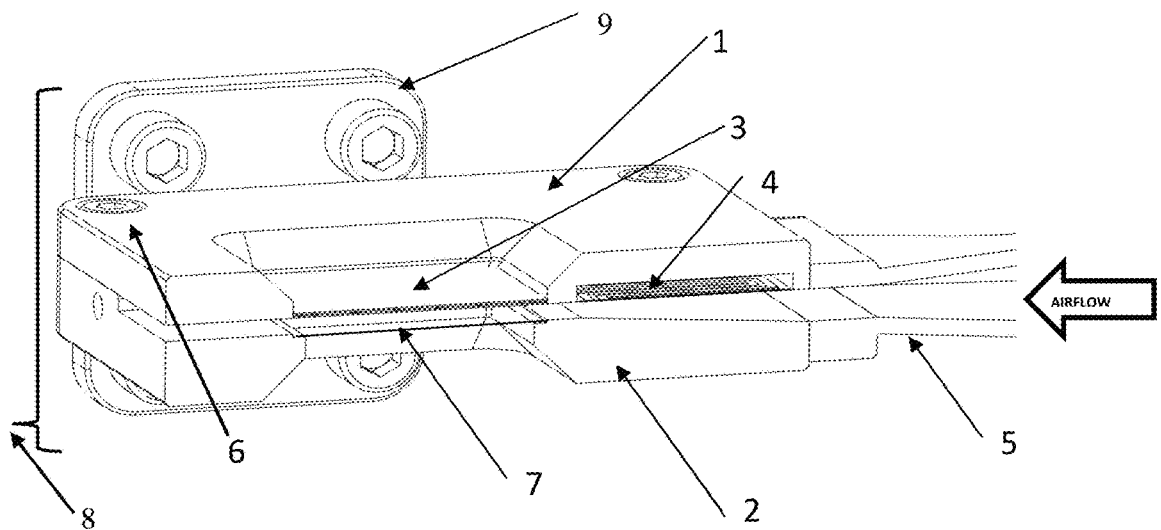
FIG. 2 is a cross sectional view of the exemplary device of FIG. 1.

FIG. 1 (exploded view) and FIG. 2 (cross section) provide an exemplary representation of a device of the present disclosure, which has been designed to suspend a microfluidic cartridge 3 in a holder (top half 1 and bottom half 2) such that fluid flow can be blown across one side of the cartridge. Microfluidic cartridge 3 has an upper side and a lower side. The top half of the cartridge holder structure 1 has an upper side and a lower side, and the bottom half of the cartridge holder structure additionally has an upper side and a lower side. Microfluidic cartridge 3 is placed between the top half of cartridge holder 1 and the bottom half of cartridge holder 2, such that the upper side of microfluidic cartridge 3 engages with the lower side of the top half of the cartridge holder structure 1, and the lower side of microfluidic cartridge 3 engages with the upper side of the bottom half of the cartridge holder structure 3. Top half of cartridge holder 1 and bottom half of cartridge holder 2 are secured together around the cartridge 3 using fixation hardware 6. When fixed together, top half of cartridge holder 1 and bottom half of cartridge holder 2 together form cartridge holder 8. Cartridge holder 8 may include viewing window 7 which enables imaging of the microfluidic cartridge 3 while in the cartridge holder 8. Cartridge holder 8 can be mounted on or within a microfluidic device or system, including a bench top system, utilizing cartridge holder mount 9. The mounting of cartridge holder 8 allows the cartridge 3 to "float" in space, such that a fluid flow can be directed across one side of cartridge 3. In one embodiment, the fluid flow comprises air or another gas. In this embodiment, a blower, fan or the like can be attached to the cooling air inlet duct 5. The blower, fan or the like can be operated by a controller, which can operate the fan in response to temperature readings, desired temperatures of the substrate or microfluidic cartridge, or in response to a desired thermal cycle. In alternative configurations, the fluid flow can be a liquid. Heating element 4 (also referred to as a preheating element) is located upstream of the cartridge 3. Cooling air inlet duct 5 is located further upstream from the heating element 4, such that the heating element 4 and the cooling air inlet duct 5 are configured such that the bulk fluid flow form the cooling air inlet duct 5 is in thermal communication with heater 4, such that heat is directed into at least a portion of the bulk fluid flow stream that is directed across one side of cartridge 3 by cooling air inlet duct 5. While FIG. 1 and FIG. 2 depict that the fluid flow is directed across the lower side of cartridge 3, alternate configurations can be provided which would direct the fluid flow along a different side, for instance, the upper side of cartridge 3. Within the fluid chamber surrounding the cartridge holder 8 and the microfluidic cartridge 3, there may be structures such as walls, baffles, and similar in order to direct the flow and maintain the flow speed across the substrate to direct the flow and maintain the flow speed across the substrate. These structures may or may not be optically transparent for imaging of the microfluidic cartridge. Modifications can be made to the exemplary structures provided herein that are within the scope of this disclosure provided enables the formation of a thermal boundary layer at the boundary of a bulk fluid flow that is supplied heat via an upstream heater and which thermal boundary layer is in thermal communication with the microfluidic cartridge or substrate, thereby allowing rapid and uniform heating and cooling of the microfluidic cartridge or substrate.

In some embodiments, the device will additionally comprise one or more temperature measuring devices (i.e., temperature probes) which can be located throughout the device, including, but not limited to in the cooling air inlet duct 5, at the heater 4, on or in the substrate or microfluidic cartridge 3, or in other advantageous positions to obtain temperature measurements that can be used to determine or estimate the temperature of the thermal boundary layer. The temperature measuring devices may be, for example, wire-like with a probe tip suspended in air. The wire may be supported by, for example, gluing or press-fitting the wire to a side of the device. Other temperature measuring device may be used, such as, for example, sensors in plastic or glass beads or other standard electronic packages. Also, in embodiments with a plurality of temperature measuring devices, the temperature measuring devices may all be of the same types or of different types. The temperature measuring device may be any suitable device known in the art for measuring temperature. The temperature measuring device may be, for example, a thermistor, thermocouple or resistance temperature detector.

In other embodiments, one or more thermal controllers may be used to control the upstream preheating element 4 and the main heater which drives the temperature dependent reactions on the microfluidic device. In some embodiments, a single controller may control both heaters, or each heater can be controlled by a separate controller. The one or more controllers can cause the temperature of the upstream preheating element 4 or the main heater to increase or decrease the temperature according to a measured temperature within the device, a desired temperature of the substrate or microfluidic cartridge 3, desired thermal cycling conditions, or any combination thereof. Further, a controller can operate a blower or fan to cause the cooling air inlet duct to provide a bulk fluid flow towards the preheating element 4 and the substrate or microfluidic cartridge 3, such that when the preheating element 4 is turned on, a thermal boundary layer is formed.

Figure 3:
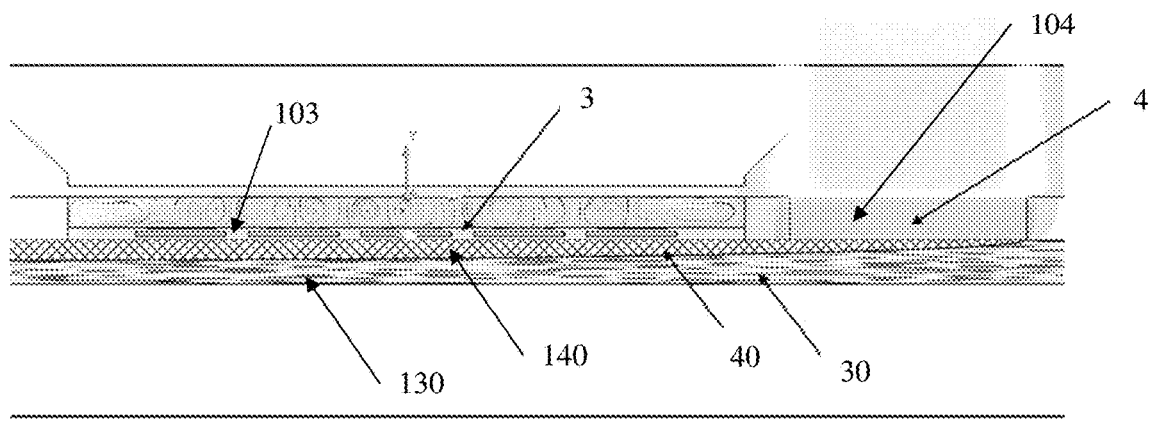
FIG. 3 is a depiction of the formation of the thermal boundary layer in the bulk fluid flow stream directed at a microfluidic cartridge within the cartridge holder.

FIG. 3 shows a cross sectional view of the device of FIGS. 1 and 2 with the theoretical fluid flow regions displayed, including a representation of the thermal boundary layer 40 formation. The cooling air inlet duct 5 (not depicted in FIG. 3) directs a bulk fluid flow 30 across a surface of the heating element 4 located and the microfluidic cartridge 3. The bulk fluid flow 30 blowing across the heating element 4, which causes a portion of the bulk fluid flow 30 at the interface or border between the bulk fluid flow and the lower surfaces of the heater 4 and microfluidic chip 3 to be in thermal communication with the heating element 4. This heating of the border area of the bulk fluid flow 30 generates a thermal boundary layer 40 (hatched in FIG. 3). The fluid film temperature ($T_{film}$) 140 in the thermal boundary layer 40 can be approximated by an average of the preheating element 4 surface temperature ($T_{preheater}$) 104 and the bulk fluid 30 temperature ($T_{fluid}$) 130. The heating of the fluid film or thermal boundary layer 40 allows for the microfluidic chip 3 temperature ($T_{cartridge}$) 103 to acclimate to that of the fluid film temperature of the thermal boundary layer to prevent thermal overshoot or undershoot of the target temperature. The small heater 4 and thermal boundary layer 40 thermal mass allows for rapid changes of the fluid temperature, allowing cooler air for rapid cooling rates and then rapidly heating the thermal boundary layer 40 for a more insulating effect, thereby minimizing thermal overshoot of the target substrate. Heating in this manner allows for accurate temperature control to be maintained via the thermal boundary layer 40 fluid film temperature, which requires significantly less power to preheat, allowing for faster temperature changes within the thermal boundary layer for more effective cooling without the need for a large heating element for the entire bulk fluid flow. It is noted that heater 4 is not directly responsible for the thermal cycling of the microfluidic cartridge 3. Rather, the thermal cycling device or system will include a second heater ("main heater") that is the primary heating source for the substrate or microfluidic cartridge 3 and that the upstream preheating element 4 is primarily used during the cooling phase of thermal cycling.

The present disclosure provides a method for cooling a substrate, wherein the substrate can be a microfluidic cartridge or other reagent container. The method comprises the steps of (i) heating a substrate by turning on a primary heating element, until such time as the substrate is heated to the desired temperature, at which time the primary heating element is turned off; and (ii) causing a fluid flow having a lower temperature than that of the substrate to flow over a surface of the substrate, causing a thermal boundary layer 40 to form, wherein the thermal boundary layer has a different temperature than that of the fluid flow. Such method allows for the rapid cooling of the substrate or microfluidic cartridge, and the method may additional comprise step (iii) providing a secondary heating element (preheating element) 4 located upstream of the substrate. The primary heating element and secondary heating element (preheating element) 4 can be controlled by one or more thermal controllers. The method of cooling a substrate can additionally comprise the step of (iv) causing the secondary heating element to heat the fluid flowing over the substrate such that the temperature of the thermal boundary layer is increased. In some embodiments, the warming of the fluid regulates the cooling of the substrate. The method can also additionally comprising the step of (v) turning off the secondary heating element after the desired substrate temperature is reached. Steps (i) to (v) can be caused to occur to occur repeatedly to provide thermal cycling of the substrate, and the thermal cycling can be repeated until amplification of a nucleic acid sample occurs.

Figure 6:
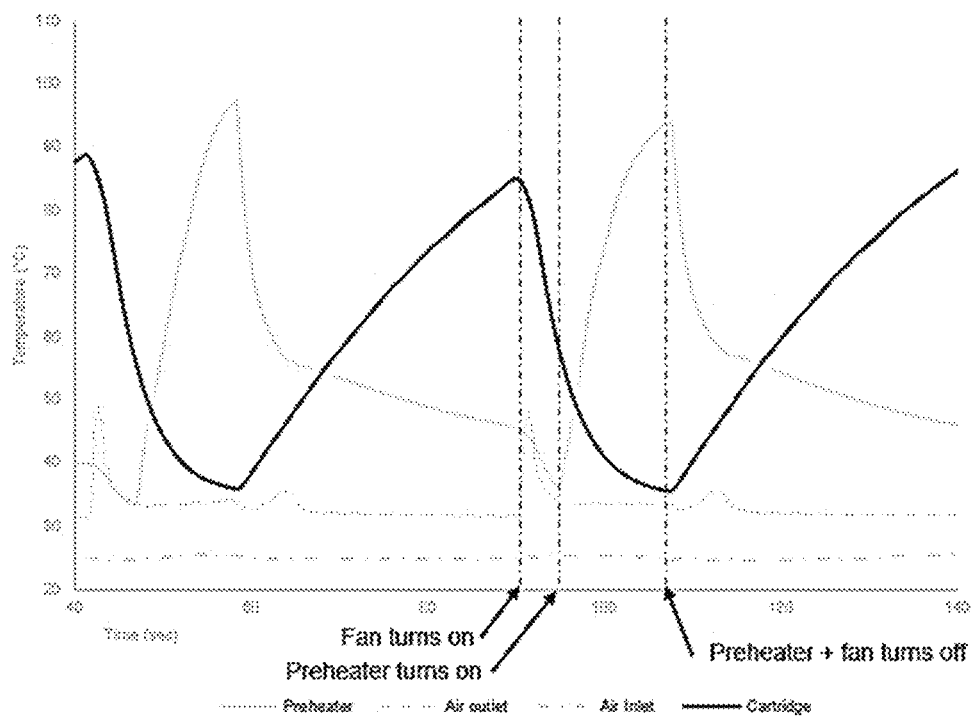
FIG. 6 is a plot of an exemplary thermal cycling sequence depicting temperature vs time.

FIG. 6 shows an exemplary diagram of a thermal cycling sequence for a device according to the present disclosure. Arrows show key points in the cycle where the fan is turned on for cooling, and after a set amount of time the upstream preheating element 4 is turned on. By cycling in this way, the device can take advantage of the rapid cooling using ambient or cooled air during the initial cooling stages, then after nearing the lower target temperature, the preheating element can be turned on to prevent thermal under/overshoot and maintain the critical annealing temperature uniformity. By heating the thin film of fluid near the substrate the power requirements are lowered significantly compared to heating the entire fluid before passing it over the chip.

The method and device described herein maintains accurate temperature control of the substrate or microfluidic cartridge via the fluid film temperature, preventing thermal overshoot or undershoot of the substrate or microfluidic cartridge from occurring as the difference between the temperature of the substrate or microfluidic chip and the desired temperature narrows.

According to the present disclosure, the method and device described herein can increase the cooling speed by using a faster fluid flow, but because the entire bulk fluid flow 30 does not have to be heated (as only the thermal boundary layer 40 is heated), the power requirements are not increased significantly.

According to a further embodiment of the present disclosure, a thermal boundary layer 40 created by heating a bulk fluid flow 30 with a preheating element 4 can be used both for cooling a substrate or microfluidic cartridge as well as for heating a substrate or microfluidic cartridge during a thermal cycling reaction. For instance, in such an embodiment, the thermal boundary layer can be heated to a temperature in between the current temperature of the substrate or microfluidic cartridge and the desired temperature to more rapidly raise the temperature of the substrate or cartridge before acting as an insulator to prevent an overshooting of the desired temperature. Similarly, the thermal boundary layer can be heated to a temperature over the desired temperature to begin rapidly raising the temperature of the substrate or cartridge before the preheating element 4 is turned off or the temperature is reduced to allow the thermal boundary layer to again act as an insulator to prevent an overshooting of the desired temperature.

The present disclosure relates to the heating and cooling of a substrate or microfluidic cartridge for thermal cycling applications, therefore, although the description and figures herein primarily relate to the heating and cooling mechanisms, it is intended that the disclosed device and method are integrated into or used with a thermal cycling device, system or method. For example, the device and method of the present disclosure can be utilized with or incorporated into known thermal cycling devices, systems or methods, including, for instance, those described in any of US20200232020, WO2020154407, U.S. Ser. No. 10/226,772, U.S. Pat. Nos. 9,919,314, 9,829,389, 9,823,135, 9,554,422, and, U.S. Pat. No. 9,542,526 the contents of which are hereby incorporated herein in their entirety.

EXAMPLE

Feasibility tests were performed where four separate conditions were tested wherein air was used as the working fluid, which was transported over the substrate via a duct system connected to an external blower. During the feasibility tests, an optical heating method was used as the main heater of the substrate, and then various conditions of cooling with and without the pre-heating element were tested to see the subsequent effects, both on cooling speed and uniformity between the fluidic chambers.

The chip used for the tests was made of a polymer material and was supplied with five separate chambers filled with deionized water, such that each one could be compared against the other for uniformity via infrared imaging. Four separate test conditions were utilized:

(1) ambient air cooling (main heater off, preheating element off);
(2) preheated air cooling (main heater off, preheating element on)
(3) ambient air cooling plus optical heating of the microfluidic chip, (main heater on, preheating element off) and
(4) preheated air cooling plus optical heating of the microfluidic chip (main heater on, preheating element on).

Figure 4:
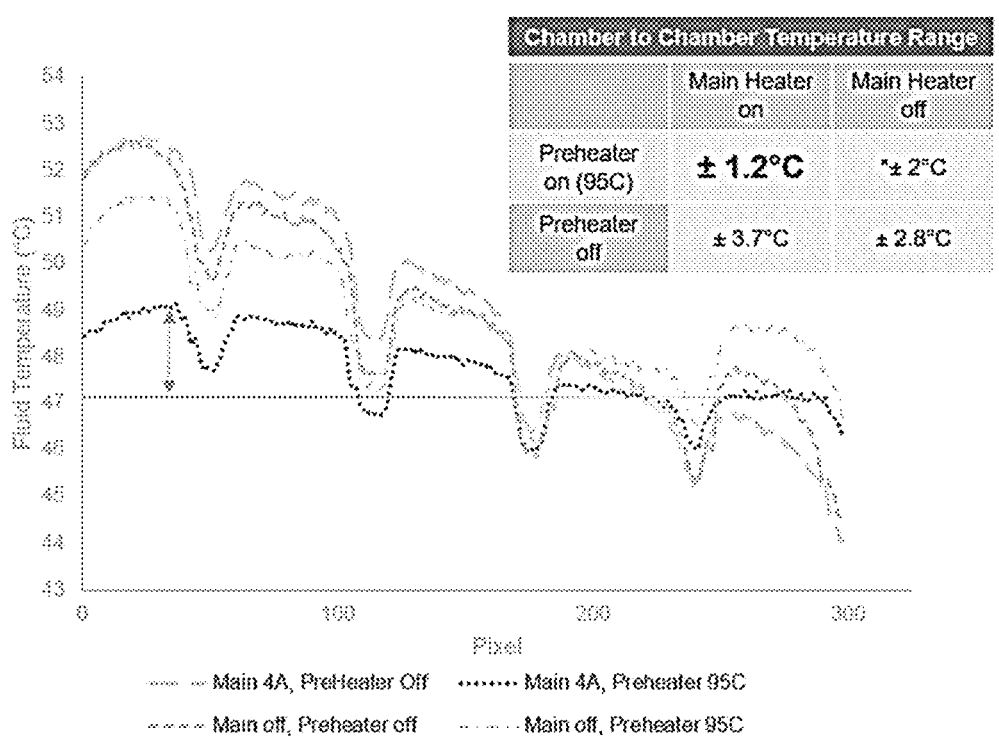
FIG. 4 is a uniformity profile showing temperature uniformity across five chip chambers during testing.
Figure 5:
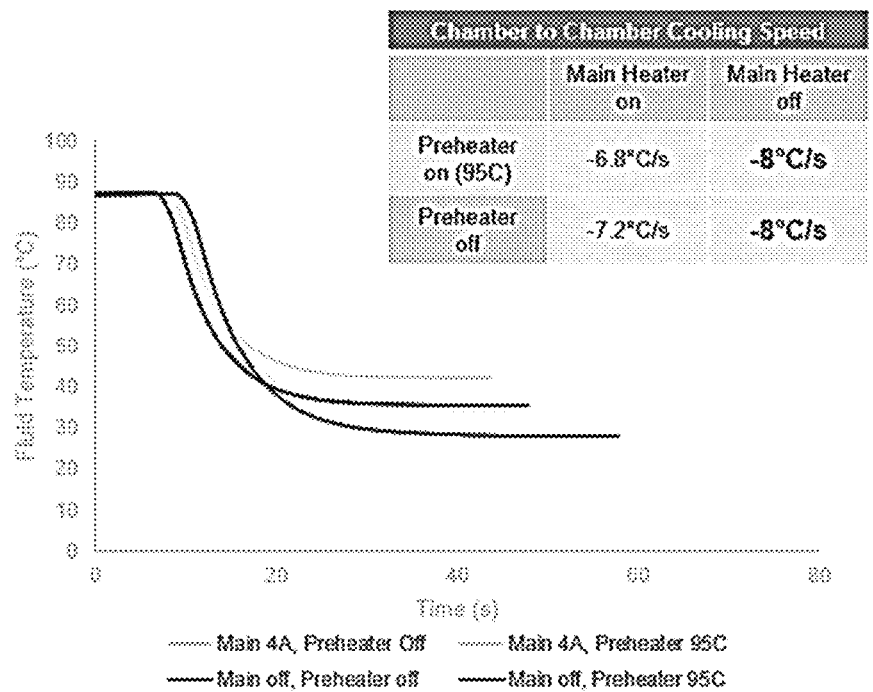
FIG. 5 is a cooling speed plot of fluid temperature vs. time.

Results are shown in FIGS. 4-6. FIG. 4 is a uniformity profile across the five separate chambers present on the substrate. Each hump of the curve represents the fluid in one of the five chambers. In FIG. 4, the chart corresponds to the bulk fluid flow (airflow) from right to left, i.e., the chamber depicted on the first right side of the plot was at the leading edge in the airflow stream. As shown in the chart and the depicted chamber to chamber temperature ranges, the smallest temperature variation between chambers occurred when both the main heater and the preheating element were used, thereby generating a thermal boundary layer in the airflow.

FIG. 5 additionally shows that uniformity was improved substantially when using the preheating method versus other methods. As shown in FIG. 5, the cooling speed was not significantly affected by the preheating. This can be explained by the lag time when turning the heater on. Inherently, the preheating element takes some time to heat up, and during this process cool air is flowing over the chip and cooling it rapidly. After several seconds, the preheating element reaches the target temperature and the preheated air acts to insulate and maintain the uniform cartridge temperatures seen. Overall, a cooling rate of 8° C./s and uniformity of ±1.2° C. was achieved with the device of the present disclosure.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred to herein as being "on", "against", "connected to", or "coupled to" another element or part, then it can be directly on, against, connected or coupled to the other element or part, or intervening elements or parts can be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, can be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device can be otherwise oriented (rotated 90 degrees or at other orientations) and the spatially relative descriptors used herein are to be interpreted accordingly. Similarly, the relative spatial terms "proximal" and "distal" can also be interchangeable, where applicable.

The term "about," as used herein means, for example, within 10%, within 5%, or less. In some embodiments, the term "about" can mean within measurement error.

The terms first, second, third, etc. can be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "includes", "including," and "containing" are to be construed as open-ended terms (i.e., meaning "including, but not limited to,") unless otherwise noted. Specifically, these terms, when used in the present specification, specify the presence of stated features, integers, steps, operations, elements, and/or components, but do not preclude the presence or addition of one or more other features, integers, steps, operations, elements, components, and/or groups thereof not explicitly stated. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

It will be appreciated that the methods and compositions of the instant disclosure can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A fluidic device comprising:
   a microfluidic cartridge comprising a substrate, wherein the substrate comprises at least one reaction chamber;
   a cartridge holder configured to form an air channel between the cartridge holder and the microfluidic cartridge;
   an air inlet duct configured to flow air into the air channel to provide fluid flow that creates a thin fluid film in thermal communication with the substrate;
   a first heating element; and,
   a second heating element;
   wherein the first heating element applies heat to the substrate, and,
   wherein the second heating element is upstream of the substrate in relation to the fluid flow from the air inlet duct, and in thermal communication with the thin fluid film.

2. The device of claim 1, wherein the second heating element is incorporated in the fluid flow upstream of the first heating element.

3. The device of claim 1, wherein the thin fluid film comprises a thermal boundary layer adjacent to a surface of the substrate.

4. The device of claim 1, wherein the second heating element is located on the same side of the substrate as the thin fluid film.

* * * * *